United States Patent [19]

Beschke et al.

[11] 4,171,445

[45] Oct. 16, 1979

[54] PROCESS FOR THE PRODUCTION OF PYRIDINE AND 3-METHYL PYRIDINE

[75] Inventors: Helmut Beschke; Heinz Friedrich; Gerd Schreyer, all of Hanau, Fed. Rep. of Germany

[73] Assignee: Deutsche Gold- und Siber-Scheideanstalt vormals Roessler, Frankfurt, Fed. Rep. of Germany

[21] Appl. No.: 622,488

[22] Filed: Oct. 15, 1975

[30] Foreign Application Priority Data

Oct. 17, 1974 [DE] Fed. Rep. of Germany ....... 2449340

[51] Int. Cl.² .......................................... C07D 213/12
[52] U.S. Cl. ..................... 546/251; 546/250

[58] Field of Search ................... 260/290 P; 546/250, 546/251

[56] References Cited

U.S. PATENT DOCUMENTS

| 3,898,177 | 8/1975 | Beschke et al. | 260/290 P |
| 3,917,542 | 11/1975 | Beschke et al. | 260/290 P |

FOREIGN PATENT DOCUMENTS 1193341  5/1970  United Kingdom ................. 260/290 P Primary Examiner—Alan L. Rotman
Attorney, Agent, or Firm—Cushman, Darby & Cushman

[57] ABSTRACT

Pyridine and 3-methyl pyridine are prepared by reacting acrolein with ammonia in the gas phase on a catalyst in a fluidized bed. The acrolein and ammonia are introduced separately in gaseous form into the reactor.

16 Claims, 1 Drawing Figure

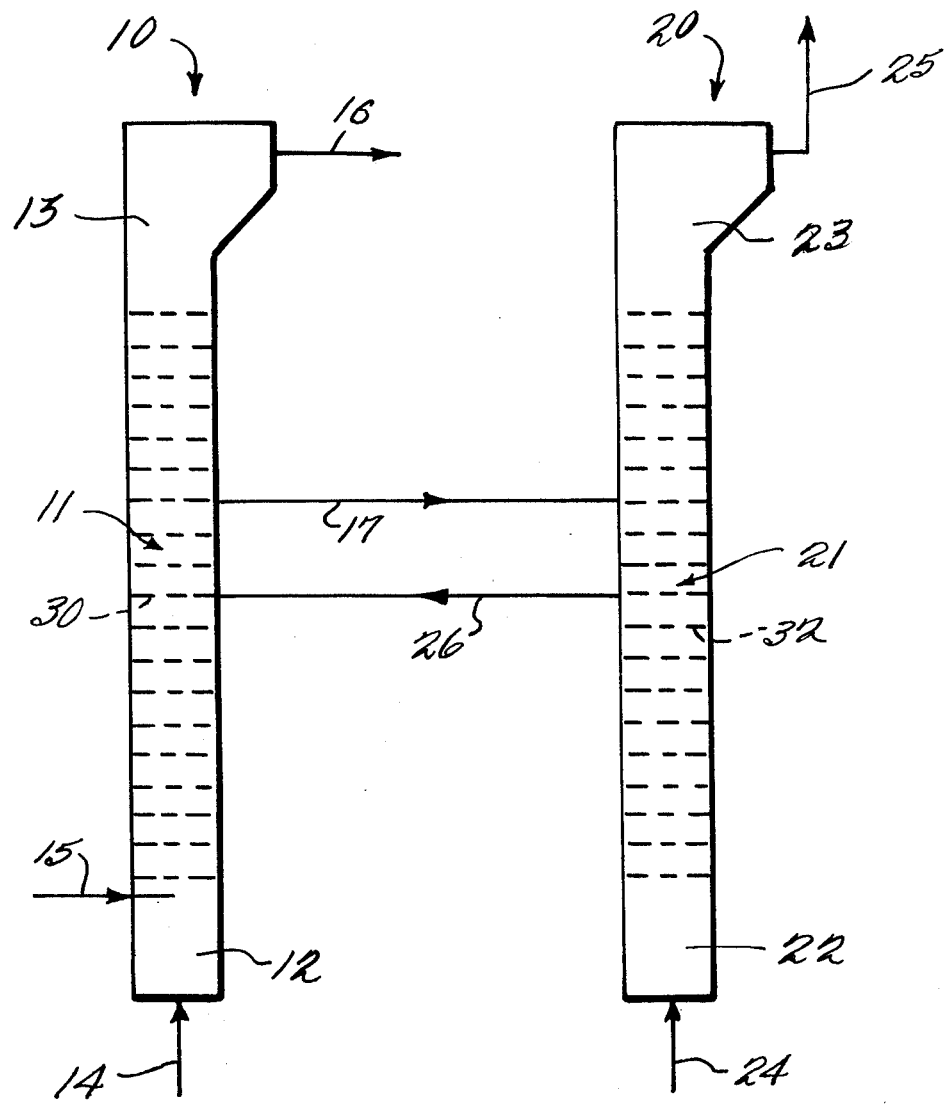

PROCESS FOR THE PRODUCTION OF PYRIDINE AND 3-METHYL PYRIDINE

The invention is directed to a process for the production of pyridine and 3-methyl pyridine by the catalytic reaction of acrolein with ammonia in the gas phase.

Several different types of process are known. They differ essentially in the particular catalysts used. As such, there are chiefly employed materials based on oxides and silicates of aluminum. Aluminum oxide or aluminum silicate containing fluorine compounds are used (Moll, German Democratic Republic Pat. No. 58 960, the entire disclosure of which is hereby incorporated by reference and relied upon), or fluosilicic acid or fluoboric acid which are pretreated by heating to 450° C. (German Offenlegungsschrift No. 1,917,037 the entire disclosure of which is hereby incorporated by reference and relied upon). There have also been used zeolitic molecular sieves containing lanthanide cations (German Offenlegungsschrift No. 2,023,158 the entire disclosure of which is hereby incorporated by reference and relied upon). The catalysts concerned are only moderately effective, the process therefore results in only low yields, based on the amount of catalyst and reaction time.

More effective catalysts are compounds of the elements Al, F and O which additionally contain at least one element of the second, third or fourth group of the periodic system (German Offenlegungsschrift No. 2,151,417 or corresponding Beschke U.S. Pat. No. 3,898,177) or at least two elements of the second, fourth, fifth or sixth group of the periodic system (German Offenlegungsschrift No. 2,224,160 or corresponding Beschke U.S. application Ser. No. 361,331 filed May 17, 1973, now U.S. Pat. No. 3,960,766), or at least one element of the second group of the periodic system (German Offenlegungsschrift No. 2,239,801 or corresponding Beschke U.S. application Ser. No. 386,570 filed Aug. 8, 1973, now U.S. Pat. No. 3,917,542) which have been pretreated at temperatures of 550° to 1200° C. The catalysts are used in fixed beds or in fluidized beds.

Beschke U.S. Pat. No. 3,898,177 describes the catalyst in claim 1 as consisting essentially of oxygen containing compounds of Al, F, at least one of the elements B and Si and at least one element from the second and fourth groups of the periodic system selected from the group consisting of Mg, Ba, Zn, Sn and Zr, said catalyst having been prepared by heating in the presence of oxygen at a temperature of 600° to 800° C.;

1. aluminum, aluminum oxide or an aluminum compound convertible to the oxide at said temperature,
2. a compound of fluorine, said fluorine having been added as ammonium fluoride, ammonium hydrogen fluoride, hydrogen fluoride, fluoboric acid, Fluosilicic acid, boron trifluoride, magnesium fluoborate, magnesium fluosilicate, zinc fluosilicate or barium fluosilicate,
3. boron, silicon, boric oxide, silica or a compound of boron or silica convertible to the oxide at said temperature and
4. magnesium, zinc, tin, zirconium, magnesium oxide, zinc oxide, tin oxide or a compound of zirconium or barium convertible to the oxide at said temperature, the atomic ratio of Al to F being from 1000:25 to 1000:800 and the atomic ratio of Al to the total of (3) and (4) being from 1000:5 to 100:200, the atomic ratio of the total of boron and silicon to the other element from the second and fourth groups being between 1 to 10 and 10 to 1.

Beschke U.S. application Ser. No. 386,570 in the generic claim describes the catalyst as having been prepared by heating at 600° to 800° C. in the presence of gaseous oxygen, (1) aluminum metal, aluminum oxide or a compound of aluminum convertible to the oxide upon heating with gaseous oxygen at 600° to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system.

Beschke U.S. application Ser. No. 361,331 in the generic claim describes the catalyst as consisting essentially of the product obtained by treating with oxygen at a temperature of 550° to 1200° C. compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1000 to 10 and 1000 to 800 and of Al to the elements of the second, fourth, fifth and sixth groups being between 1000 to 5 and 1000 to 200.

As stated, however, Beschke U.S. Pat. No. 3,898,177 and Beschke U.S. application Ser. No. 386,570 also disclose a pretreatment temperature range of 550° to 1200° C.

There has now been found a process for the production of pyridine and 3-methyl pyridine by reacting acrolein with ammonia in the gas phase on a catalyst in a fluidized bed reactor which is characterized in that acrolein and ammonia are led into the reactor in gaseous form separately from each other. Customarily the reaction gases are mixed with each other prior to entering the fluidized bed. By employing separate gas streams according to the invention which means that ammonia and acrolein first come into contact with each other inside the fluidized bed, there is produced a substantially higher yield based on the amount of catalyst and reaction time.

In carrying out the process of the invention acrolein and ammonia are added in gaseous form as is customary. In general for each mole of acrolein there is used at least 1 mole of ammonia. It is advantageous to use acrolein and ammonia in the molar ratio of from 1.0 to 1.0 up to 1.0 to 3.0, especially from 1.0 to 1.3 up to 1.0 to 2.5. Suitably there is additionally introduced an inert gas, especially nitrogen. Advantageously there is used 0.5 to 3.0 moles of inert gas per mole of acrolein. Preferably 1.0 to 2.5 moles of inert gas are employed per mole of acrolein. Other inert gases include, for example, argon or helium. The inert gas is fed in either entirely or partially separately or it is mixed with either the acrolein or the ammonia. Preferably the inert gas is introduced in an amount of 1/20 to about 1/5 of its entire amount with the acrolein and the balance with the ammonia. By the ratio of ammonia and inert gas in the entire amount there can be in a given case regulated to a certain extent whether the formation of pyridine or 3-methyl pyridine is favored. In general at high ammonia content there is preferably produced pyridine and at high inert gas content preferably 3-methyl pyridine.

As catalysts there can be employed all materials which are able to catalyze the reaction of acrolein with ammonia to form pyridine and 3-methyl pyridine and which can be used in a fluidized bed. Preferably there are employed the catalyst made in accordance with German Offenlegungsschrift No. 2,151,417, Beschke U.S. Pat. No. 3,898,177 German Offenlegungsschrift No. 2,224,160, Beschke U.S. application Ser. No. 361,331, German Offenlegungsschrift No. 2,239,801 and Beschke U.S. application Ser. No. 386,570. These catalysts are especially suitable if they are produced on a foundation of aluminum oxide which has a surface area (BET) between 80 and 400 m$^2$/g and besides suitably have a pore volume of 30 to 60 100 grams, an average pore diameter of 50 to 200×10$^{-7}$ mm and a breaking strength of 10 to 100 N (Newton). The catalysts are used in the customary particle size for fluidized bed processes. Preferably there are used particles having a size of 0.1 to 3.0 mm., especially 0.2 to 2.0 mm.

The reaction takes place at temperatures between 300° and 500° C., preferably between 380° and 480° C. The pressure can be selected at random as desired, however, it is recommended in order to use simple apparatus to use normal pressure or only moderately lower or elevated pressure up to about 3 bar. A slightly reduced pressure or superatmospheric pressure in a given case results if the gases are sucked through the apparatus or pressured through the apparatus.

In carrying out the process, there are employed fluidized bed reactors of customary construction. However, these reactors are so designed that acrolein and ammonia can be fed in separately from each other so that these gates first meet in the fluidized bed.

The gas led from below into the reactor to form the catalyst fluidized bed can at will be chosen from the inert gas, the acrolein alone, the ammonia alone or a mixture of acrolein with inert gas or a mixture of ammonia with inert gas. The gas portion of acrolein, ammonia and inert gas which is not led into the reactor from below is fed into the fluidized bed at another place or at several places. However, acrolein and ammonia must always be separated from each other. The distribution of the gas stream is adjusted in a given case according to the construction of the reactor. Preferably the ammonia is led into the reactor from below and the acrolein is led into the fluidized bed.

The resulting reaction mixture is withdrawn from the reactor suitably from the upper portion thereof and the pyridine and 3-methyl pyridine recovered therefrom in customary manner, for example, by gas washes, extractive working up of the washing liquid and distillation.

The catalyst from time to time requires regeneration. For this purpose with advantage, especially with the catalysts of German Offenlegungsschrift No. 2,151,417, Beschke U.S. Pat. No. 3,898,177, German Offenlegungsschrift No. 2,224,160, Beschke U.S. application Ser. No. 361,331, German Offenlegungsschrift No. 2,239,801 and Beschke U.S. application Ser. No. 386,570, the catalyst is treated with oxygen or an oxygen containing gas, preferably air, namely at approximately the temperature at which the reaction of acrolein with ammonia takes place. This treatment of the catalyst can take place while oxygen or an oxygen containing gas is led through the reactor instead of acrolein and ammonia. Also, the catalyst, in a given case in portions, can be conveyed into a regenerator and treated in this in a corresponding manner.

The process of the invention can be carried out, for example, in a process according to the drawing. This kind of process is recommended preferably when using the catalysts of German Offenlegungsschrift No. 2,151,417, Beschke U.S. Pat. No. 3,898,177, German Offenlegungsschrift No. 2,224,160, Beschke U.S. application Ser. No. 361,331, German Offenlegungsschrift No. 2,239,801 and Beschke U.S. application Ser. No. 386,570.

The single FIGURE of the drawing is a schematic illustration of an apparatus suitable for carrying out the invention.

Referring more specifically to the drawing, there is used a tubular reactor 10 provided with cooling and heating devices (not shown). The reactor suitably contains in the middle portion 11 gas distribution plates 30, but in the lower part 12 and the upper part 13 there is free space. The first reaction gas is led into the reactor from below through line 14 and so regulated that the catalyst in the reactor forms a fluidized bed. The other reactant gas is led through line 15 into the fluidized bed. The reaction mixture is drawn off from the reactor in the upper part thereof through the line 16. A portion of the catalyst is always transported via line 17 from the reactor 10 to a regenerator 20. This regenerator also is advantageously constructed similar to the reactor 10. The regenerator also suitably contains gas distribution plates 32 in the middle portion 21, but there is free space in the lower portion 22 and in the upper portion 23. The oxygen or oxygen containing gas is led into the regenerator 20 from below through line 24. The gas flow is so regulated that the catalyst present in the regenerator forms a fluidized bed. The gas escaping from the regenerator via line 25 is discarded. A portion of the catalyst is continuously relieved from the regenerator 20 via line 26 into the reactor 10.

A preferred operating procedure is to use a reactor in which the space 11 contains the gas distribution plates is 3 to 20 times as high, preferably 5 to 12 times as high, as the free space 12 below the plates. The gas distribution plates advantageously consist of wire screens. Their mesh size is adjusted according to the particle size of the catalyst and is suitably 2 to 20 times as large, especially 3 to 12 times as large, as the diameter of the largest catalyst particles. The vertical distance between the wire screens suitably is 1 to 20 cm., especially 2 to 10 cm.

The gas flow, in a given case through addition of inert gas, is advantageously so fixed to the cross-section of the reactor that the catalyst fluidized bed reaches the upper limit of the space 11 provided with the gas distribution plates and only leaves free the space 13. The gas velocity hereby preferably is 1.5 to 5 times, especially 2.0 to 4 times the velocity required to make the particles flow.

The ammonium, in a given case diluted with inert gas, is led into the reactor from below; the acrolein in liquid form fed into a connected evaporator, vaporized there and diluted with nitrogen and then led into the reactor 10 in one place or in several places in the lower free space 12, e.g., in the middle third of this space. The feeding of the acrolein is suitably so chosen that reaction mixture leaving the reactor via line 16 is as free as possible of acrolein and preferably contains no free acrolein. There is generally employed for each part of catalyst in the reactor 0.1 to 2.0, especially 0.4 to 1.6 parts by weight of acrolein per hour.

The amount of catalyst which is led to the regenerator can be as large as desired. However, suitably it is 5 to 500% of the total amount of catalyst in the reactor, especially 10 to 250%, per hour. It can be advantageous to use a regenerator which is of the same size and construction as the reactor. In this case, it is generally suitable to so regulate the amount of catalyst that there is present about an equal amount of catalyst in the reactor and in the regenerator. The temperature in the regenerator is preferably a little lower, especially 10° to 30° C. lower, than the temperature in the reactor.

Unless otherwise indicated, all parts and percentages are by weight.

EXAMPLE 1

There was used equipment according to the drawings. Reactor 10 and regenerator 20 consisted of tubes 70 mm. wide which had in their lower portions a free space 12 or 22 which was 200 mm. high; thereover at intervals of 50 mm., 40 wire screens (30 and 32) each in the spaces 11 and 21. The wire screens had an interval between meshes of 5 mm. There were provided free spaces 13 and 23 having a height of 600 mm. and a width up to 160 mm.

There were led into the reactor 10 in gaseous form in uniform flow hourly from below via line 14 a gas mixture of 1500 normal liters (i.e., measured at standard pressure and temperature) of nitrogen and 2150 normal liters of ammonia and from the side via line 15 there were led into the fluidized layer 130 mm. above the bottom of the reactor from an acrolein evaporator a gas mixture of 2700 grams of acrolein and 210 normal liters of nitrogen. The reactor contained 2.0 kg of catalyst which was produced according to Beschke U.S. application Ser. No. 386,570 (and German Offenlegungsschrift No. 2,239,801) example 4 from aluminum oxide, magnesium nitrate ammonium hydrogen fluoride and had an atomic ratio of aluminum to magnesium to fluorine of 1000:50:100. The catalyst had a particle size between 0.4 and 1.0 mm. The temperature in the reactor was held at 460° C. The reaction mixture leaving via line 16 and which was free of acrolein was led at a temperature of 250° C. into a gas washing apparatus in which pyridine and 3-methyl pyridine were washed out by means of water. The remaining residual gas of ammonia and nitrogen was recycled into the reactor.

The regenerator 20 contained an additional 2.0 kg of the catalyst. There were introduced into the regenerator from below hourly 3000 normal liters of air. The temperature in the regenerator was held at 440° C. In a steady stream there were transferred hourly from the reactor to the regenerator 1.4 kg of catalyst and likewise there were returned 1.4 kg from the regenerator to the reactor.

The acrolein reaction was 100%. There were recovered hourly 426 grams of pyridine and 1042 grams of 3-methyl pyridine. This corresponds to a pyridine yield of 22.4% and a 3-methyl pyridine yield of 46.7% based on the acrolein added. The yield amounted to 734 grams of pyridine and 3-methyl pyridine per kg of catalyst in the reactor per hour.

EXAMPLE 2

The procedure was the same as in Example 1, but instead of supplying 2700 grams of acrolein hourly, there were fed only 2160 grams of acrolein per hour. The acrolein reaction was 100%. There were recovered hourly 378 grams of pyridine and 870 grams of 3-methyl pyridine. This corresponds to a pyridine yield of 24.8% and a yield of 3-methyl pyridine of 48.5% based on the acrolein added. The yield amounted to 624 grams of pyridine and 3-methyl pyridine per kg of catalyst in the reactor per hour.

The process can comprise, consist essentially of or consist of the steps set forth and the materials employed can comprise, consist essentially of or consist of those set forth.

What is claimed is:

1. In a process for the production of pyridine and 3-methyl pyridine by reaction of acrolein with ammonia in the presence of an inert gas in the gas phase on a catalyst in a fluidized bed in a reactor the improvement comprising introducing the acrolein and ammonia in gas form separately into the reactor.

2. The process of claim 1 wherein one of the acrolein and ammonia is introduced into the reactor from below the fluidized bed and the other of said acrolein and ammonia is introduced into the fluidized bed.

3. The process of claim 2 wherein the ammonia is introduced into the reactor from below and the acrolein is introduced into the fluidized bed.

4. The process of claim 3 wherein at least one of said acrolein and ammonia is introduced into the reactor admixed with an inert gas.

5. The process of claim 1 wherein at least one of said acrolein and ammonia is introduced into the reactor admixed with an inert gas.

6. The process of claim 1 wherein the catalyst is one which has been prepared by heating compounds consisting essentially of the elements Al, F and O, at least one of B and Si and at least one of Mg, Ba, Zn, Sn and Zr with oxygen at a temperature of 550° to 1200° C.

7. The process of claim 1 wherein the catalyst is one which has been prepared by heating compounds consisting essentially of the elements Al, F and O and at least one element of the second main group of the periodic system at a temperature of 550° to 1200° C.

8. The process of claim 1 wherein the catalyst is one which has been prepared by heating compounds consisting essentially of the elements Al, F and O and at least two other elements selected from the group consisting of Mg, Ba, Zr, Sn, Ti, P, Ta, Sb and S at a temperature of 55° to 1000° C.

9. The process according to claim 1 wherein there is employed 0.5 to 3.0 moles of inert gas per mole of acrolein.

10. The process according to claim 9 wherein there is employed 1.0 to 3.0 moles of ammonia per mole of acrolein.

11. The process according to claim 10 wherein 1/20 to 1/5 of the inert gas is introduced with the acrolein and the balance with the ammonia.

12. The process according to claim 11 wherein the temperature is between 300° and 500° C.

13. The process according to claim 9 wherein 1/20 to 1/5 of the inert gas is introduced with the acrolein and the balance with the ammonia.

14. The process according to claim 1 wherein 1/20 to 1/5 of the inert gas is introduced with the acrolein and the balance with the ammonia.

15. The process of claim 1 wherein the temperature is between 300° and 500° C.

16. The process of claim 1 wherein the gases introduced to the reactor consist of ammonia, acrolein and inert gas.

* * * * *

UNITED STATES PATENT AND TRADEMARK OFFICE
CERTIFICATE OF CORRECTION

PATENT NO. : 4,171,445
DATED : October 16, 1979
INVENTOR(S) : BESCHKE, Helmut, FRIEDRICH, Heinz and SCHREYER, Gerd It is certified that error appears in the above—identified patent and that said Letters Patent is hereby corrected as shown below:

Column 3, line 14, change "60 100" to --60 ml/100--.

Column 4, line 38, before "contains" insert --which--.

Signed and Sealed this

First Day of July 1980

[SEAL]

Attest:

SIDNEY A. DIAMOND

Attesting Officer

Commissioner of Patents and Trademarks